United States Patent [19]

Ueoka et al.

[11] Patent Number: 4,725,291
[45] Date of Patent: Feb. 16, 1988

[54] METHOD OF COLLECTING PYROMELLITIC ANHYDRIDE

[75] Inventors: Masatoshi Ueoka, Himeji; Hiroshi Yoshida, Toyonaka; Atsushi Ohkubo; Shinya Tanaka, both of Himeji, all of Japan

[73] Assignee: Nippon Shokubai Kagaku Kogyo Co., Ltd., Osaka, Japan

[21] Appl. No.: 26,895

[22] Filed: Mar. 17, 1987

[51] Int. Cl.$^4$ ............................................. B01D 7/02
[52] U.S. Cl. .................................... 55/82; 549/239; 560/78
[58] Field of Search .................... 55/82; 549/239, 250; 560/78

[56] References Cited

U.S. PATENT DOCUMENTS

| 2,803,311 | 8/1957 | Guidi | 55/82 X |
|---|---|---|---|
| 3,328,428 | 6/1967 | McMahon | 549/239 |
| 3,609,943 | 10/1971 | Richter | 55/82 |
| 4,014,755 | 3/1977 | Richter | 549/239 X |
| 4,036,594 | 7/1977 | Ibing et al. | 55/82 X |
| 4,119,645 | 10/1978 | Auroy et al. | 549/250 X |
| 4,252,545 | 2/1981 | Haferkorn | 55/82 |
| 4,435,581 | 3/1984 | Miserlis | 549/250 X |
| 4,598,157 | 7/1986 | Scharf | 549/239 |

FOREIGN PATENT DOCUMENTS

| 2009086 | 9/1970 | Fed. Rep. of Germany | 549/239 |
|---|---|---|---|
| 35253 | 10/1973 | Japan | 549/239 |

*Primary Examiner*—Robert Spitzer
*Attorney, Agent, or Firm*—Sherman and Shalloway

[57] ABSTRACT

A method of collecting pyromellitic anhydride, which comprises introducing a high-temperature gas containing pyromellitic anhydride together with an inert cooling gas into an empty column-type collecting device whose wall temperature is maintained at 150° to 200° C., effecting heat exchange between the high-temperature gas and the cooling gas in the collecting device to lower the temperature of the high-temperature gas to 150° to 200° C., thereafter passing the gaseous mixture through the collecting device at an average linear gas velocity of 0.05 to 0.5 m/sec with an average residence time to 5 to 60 seconds, and recovering needle-like crystals of pyromellitic anhydride from the bottom of the collecting device.

5 Claims, No Drawings

METHOD OF COLLECTING PYROMELLITIC ANHYDRIDE

This invention relates to a method of collecting pyromellitic anhydride from a high-temperature gas containing pyromellitic anhydride. More specifically, this invention relates to a method of collecting pyromellitic anhydride as highly pure crystals from a high-temperature gas containing pyromellitic anhydride formed by catalytic vapor-phase oxidation or a mixed high-temperature gas composed of pyromellitic anhydride formed in the purification of pyromellitic anhydride by sublimation and a carrier gas by directly subjecting the high-temperature gas to heat-exchange with an inert cooling gas under specific conditions.

Pyromellitic anhydride has recently attracted attention as an important industrial product useful as a raw material for thermally stable resins such as polyimides or for thermally stable curing agents or plasticizers for epoxy resins.

In the prior art, pyromellitic anhydride is produced by catalytic vapor-phase oxidation of durene (1,2,4,5-tetramethylbenzene) or another 1,2,4,5-tetraalkylbenzene with molecular oxygen. Since in this vapor-phase oxidation reaction, pyromellitic anhydride is obtained as a gaseous mixture having a high temperature, it is necessary to collect pyromellitic anhydride from the gaseous mixture. In the purification of pyromellitic anhydride by sublimation, it is necessary to collect pyromellitic anhydride from a gaseous mixture composed of pyromellitic anhydride and a carrier gas.

Industrial separation and collection of pyromellitic anhydride from such a high-temperature gaseous mixture containing pyromellitic anhydride is carried out in the prior art by an indirect cooling method in which the high-temperature gaseous mixture is spontaneously or forcibly cooled to precipitate pyromellitic anhydride as crystals on the wall surface of a cooling device, or a direct cooling method involving introducing a cooling gas or liquid into the high-temperature gaseous mixture to effect gas-liquid contact.

Specifically, the indirect cooling method is carried out, for example, by precipitating crystals of pyromellitic anhydride while passing a high-temperature reaction gas containing pyromellitic anhydride over a cooling surface heated at 130° C. at a flow rate of 1 to 3 m/sec. (U.S. Pat. No. 4,252,545), or by maintaining the above reaction gas at a temperature of 230° to 150° C. and precipitating crystals of pyromellitic anhydride on a cooling surface. According to this indirect cooling method, the crystals precipitate on the cooling surface and all or part of the crystals remain on it. To take out these crystals without using a solvent, a shaving tool or a brush is required. When such a tool is used, a condenser having folds cannot be used, and a sublimation chamber is necessary. This results in an increase in the size of the collecting device and becomes uneconomical. On the other hand, a collecting device including a condenser having folds is of small-sized. But since this requires a step of separating and purifying crystals from a solvent solution thereof and the entire process becomes complex.

It is known that the aforesaid direct cooling method is carried out for example, by cooling a high-temperature reaction gas containing pyromellitic anhydride with cold water or cold air and collecting the precipitated crystals with a collector such as a bag filter (U.S. Pat. No. 3,328,428); cooling the reaction gas with cold air, collecting the crystals, burning by-products contained in the waste gas, and the supplying part of the waste gas to the reactor (U.S. Pat. No. 4,598,157); or contacting the reaction product gas containing pyromellitic anhydride with solid balls carried on air to absorb heat by these balls, precipitating the crystals of pyromellitic anhydride on the surface of the balls, and then collecting these crystals (U.S. Pat. No. 3,328,428). When in the method disclosed in U.S. Pat. No. 3,328,428, the reaction gas is cooled with cold water, part of pyromellitic anhydride changes to pyromellitic acid and consequently, the anhydride cannot be obtained in high purity. Pyromellitic anhydride of such a low purity must be dehydrated in advance when used, for example, in the production of polyimides. When it is cooled with cold air, pyromellitic anhydride of high purity cannot be obtained under the collecting conditions disclosed in this U.S. Patent, and the collecting efficiency is not entirely satisfactory. Furthermore, when the crystals are collected by using a collector such as a bag filter, clogging of the bag filter and pressure drop occur, and the device is difficult to operate continuously without using a spare collecting device. In particular, when the device is large in size, withdrawing of the crystals is a cumbersome problem. On the other hand, the method disclosed in U.S. Pat. No. 4,598,157 has the advantage that the required heat transmitting surface can be decreased by cooling with air. However, since the oxygen concentration decreases owing to the waste gas reycled to the reaction system, the life of the catalyst as the reaction yield are likely to be reduced.

Thus, conventional methods of collecting pyromellitc anhydride have various defects and have not proved to be entirely satisfactory for industrial practice.

It is an object of this invention therefore to provide a method of collecting pyromellitic anhydride of high purity with a high collection efficiently continuously from a high-temperature gas containing pyromellitic anhydride using a single small-sized collecting device. Another object of this invention is to provide a method in which the step of separating and purifying pyromellitic anhydride can be simplified.

The present inventors have studied the correlation of the operating conditions for a collecting device, i.e. the linear speed and residence time of the gaseous mixture, the cooling temperature, the temperature of the wall of the collecting device and the structure of the collecting device to the purity of the resulting pyromellitic anhydride, the efficiency of its collection and the method of withdrawing the resulting crystals in the method of crystallizing pyromellitic anhydride and collecting it from a high-temperature gas containing pyromellitic anhydride, particularly in the method of collecting and purifying pyromellitic anhydride by directly mixing a high-temperature reaction gas containing pyromellitic anhydride with an inert cooling gas to cool the reaction gas. Consequently, the present inventors have found that by selecting specific operating conditions, high-purity pyromellitic anhydride which does not substantially require subsequent purification can be collected in a high yield nearly equal to the theoretical collecting ratio at the collecting temperature calculated from the vapor pressure without involving crystallization or condensation of trimellitic anhydride, dimethylphthalic anhydride, maleic anhydride and water formed by the reaction which are impurities contained in the high-temperature gas containing pyromellitic anhydride.

Thus, according to this invention, there is provided a method of collecting pyromellitic anhydride, which comprises introducing a high-temperature gas containing pyromellitic anhydride together with an inert cooling gas into an empty column-type collecting device whose wall temperature is maintained at 150° to 200° C., effecting heat exchange between the high-temperature gas and the cooling gas in the collecting device to lower the temperature of the high-temperature gas to 150° to 200° C., thereafter passing the gaseous mixture through the collecting device at an average linear gas velocity of 0.05 to 0.5 m/sec with an average residence time to 5 to 60 seconds, and recovering needle-like crystals of pyromellitic anhydride from the bottom of the collecting device.

The high-temperature gas ontaining pyromellitic anhydride to which the method of this invention is applicable is, for example, a gaseous mixture containing pyromellitic anhydride which is a product of oxidation reaction of durene or another 1,2,4,5-tetraalkylbenzene with molecular oxygen in the vapor phase in the presence of a catalyst, or a gaseous mixture of pyromellitic anhydride and an inert gas such as nitrogen which is formed during purification of pyromellitic anhydride by sublimation, preferably the former. Generally, pyromellitic anhydride is produced by oxidizing durene in the vapor phase with a molecular oxygen-containing gas at a reaction temperature of 300° to 500° C. and a space velocity of 3000 to 15000 hr$^{-1}$ in the presence of a vanadium pentoxide-containing catalyst such as $V_2O_5$-$TiO_2$, $V_2O_5$-$TiO_2$-$P_2O_5$, $V_2O_5$-$TiO_2$-$MoO_3$ and $V_2O_5$-$TiO_2$-$Na_2O$ while the concentration of the starting durene is maintained at 10 to 50 g/Nm$^3$ of the starting gas. The high-temperature reaction gas obtained by this reaction contains no small amounts of by-products such as trimellitic anhydride, dimethylphthalic anhydride and maleic anhydride in addition to the desired pyromellitic anhydride. The method of this invention is most effectively applied when it is desired to collect high-purity pyromellitic anhydride at a high collection ratio from a high-temperature gas containing such crude pyromellitic anhydride.

The most characteristic feature of the present invention is that by using the aforesaid collecting conditions, pyromellitic anhydride can be collected as cotton-like or needle-like fine crystals. U.S. Pat. Nos. 3,328,428 and 4,598,157 disclose a method of crystallizing pyromellitic anhydride by introducing cold air into a high-temperature reaction gas containing pyromellitic anhydride. However, mere application of this method cannot result in collection of pyromellitic anhydride of high purity at a high collecting ratio. If the only purpose is to obtain highly pure crystals without consideration to the collecting ratio, it is naturally most effective to crystallize pyromellitic anhydride at the dew point determined by the concentration of pyromellitic anhydride in the high-temperature reaction gas (usually the impurities in the reaction gas obtained by vapor-phase oxidation reaction have lower boiling points than pyromellitic anhydride), or at lower temperatures. If it is still desired to increase the collecting ratio under these conditions, a very long collecting device such as to crystallize most of the uncrystallized pyromellitic anhydride is required. Alternatively, when small-size collecting device is used, the amount of the gas treated in it naturally becomes small.

On the other hand, when the only purpose is to increase the collecting ratio, it is advantageous to maintain the temperature of the collecting device at lower points than the dew point of pyromellitic anhydride. In this case, the impurities in the reaction gas are also condensed or crystallized, and the resulting crystals cannot have high purity.

After a consideration of the foregoing facts, the present invention makes it essential to cool the high-temperature reaction gas containing pyromellitic anhydride at a temperature in the range of 150° to 200° C. and maintain the inside temperature of the collecting device also at these temperatures.

When pyromellitic anhydride is crystallized by introducing cold air into the high-temperature reaction gas containing pyromellitic anhydride, the pyromellitic anhydride crystals may sometimes grow on the inner wall of the collecting device depending upon the collecting conditions. If this collecting device is a vertical empty column-type collecting device having no fin, the crystals may adhere in layer to its inner wall to clog the pipings, reduce the heat exchange efficiency and hamper continuous efficient collection of pyromellitic anhydride. For example, when an indirect cooling method is employed as in Comparative Example 1 hereinbelow in which a vertical empty column-type collecting device is used and without using an inert cooling as, the high-temperature reaction gas is cooled with the wall of the collecting device, pyromellitic anhydride adheres to the wall of the collecting device and cannot be recovered smoothly from the bottom of the collecting device. In the case of the direct cooling method using an inert cooling gas, the same phenomenon occurs more or less depending upon the operating conditions. The crystals obtained by such a method should be pulverized prior to use as a raw material for polyimides. Furthermore, the temperature of the reaction gas obtained by vapor-phase oxidation reaction is usually 300° to 500° C. When this reaction gas is abruptly cooled to a temperature considerably lower than the temperature of the reaction gas, part of pyromellitic anhydride becomes ultrafine crystals, or a mist and cannot be completely collected even when it is introduced into water.

After a consideration of the foregoing facts, the present invention makes it essential to maintain the temperature of the inside wall of the collecting device at 150° to 200° C., and to pass a gaseous mixture consisting of a high-temperature gas containing pyromellitic anhydride and an inert cooling gas through the collecting device at an average linear gas velocity of 0.05 to 0.5 m/sec and with an average residence time of 5 to 60 seconds.

Examples of the inert cooling gas that can be used in this invention include air, nitrogen, carbon dioxide, argon, a waste gas left after collection of pyromellitic anhydride from the catalytic vapor-phase oxidation reaction gas, and a waste gas resulting from various treatments of the above gases. Air is preferred. The temperature of the gas may be below the dew point of pyromellitic anhydride, but is preferably room temperature if it is desired to reduce its amount and the treatment of the waste gas.

In collecting pyromellitic anhydride by crystallization, the size and shape of the resulting crystals exert important influences on the purity of the final product and the collecting efficiency. When the gaseous mixture of the high-temperature gas containing pyromellitic anhydride and the inert cooling gas is introduced into the empty tower-type collecting device at an average linear gas velocity of 0.05 to 0.5 m/sec and a crystallization temperature of 150° to 200° C. with an average residence time of 5 to 60 seconds, pyromellitic anhydride are precipitated as cotton-like or needle-like fine crystals having a purity of at least 99%. These crystals do not adhere to, or gather on, the inside wall of the collecting device but entirely fall spontaneously onto the bottom of the device. Furthermore, these crystals are not carried away from the device by entraining gases such as nitrogen, oxygen and carbon dioxide gas contained in the reaction gas. It is unnecessary therefore in the method of this invention to provide a recovery device such as a bag filter following the collecting device.

Another advantage of the method of this invention is that since the resulting pyromellitic anhydride is in the form of cotton-like or needle-like fine crystals, it can be used directly as a raw material for polyimides, epoxy resins, polyester resins, etc. without pulverizing it. Furthermore, since the collecting device is of a vertical empty column type, the crystals can be withdrawn easily. Since the crystals can be continuously collected, no spare collecting device is required. According to the method of the invention, no heat transmitting surface is required and the collecting device can be of small-size since the high-temperature reaction gas is cooled with the inert gas. The installation cost is low because the collecting device is of the empty column-type. Still another advantage of the invention is that since purification is carried out simultaneously with the collection, the step of separation and purification of pyromellitic anhydride can be simplified.

The following examples illustrate the present invention in greater detail. It should be understood that the present invention is not limited to these examples.

EXAMPLES 1-11 and COMPARATIVE EXAMPLE

In Examples 1 to 3 and Comparative Example, durene (1,2,4,5-tetramethylbenzene) was oxidized in the vapor phase with air in the presence of a $V_2O_5$-$TiO_2$ type catalyst. Then, the reaction product gas was cooled to 250° C. and introduced at a flow rate of 4909 Nl/hr together with an inert gas maintained at 25° C. at a predetermined flow rate into a SUS 316 empty column-type collecting device having a diameter of 250 mm and a height of 2000 mm and kept at a suitable temperature by an external jacket. The reaction product gas consisted of 92.30 g/hr of pyromellitic anhydride, 5.10 g/hr of trimellitic anhydride, 0.38 g/hr of dimethylphthalic anhydride, 1.95 g/hr of maleic anhydride and 0.25 g/hr of other substances. Gas withdrawing ports are provided at positions 350, 1500 and 1500 mm away from the gas inlet part. By changing the gas withdrawing port, the residence time of the gas in the collecting device was changed.

In Examples 4 to 10, the same gas as above consisting of the reaction product gas and the inert gas was introduced into a SUS 316 empty column-type collecting device having a diameter of 250 mm and a height of 4,000 mm and kept at a suitable temperature by an external jacket. Gas withdrawing ports were provided at positions 2170 and 3630 mm away from the gas inlet part, and by changing the gas withdrawing port used, the residence time of the gas within the collecting device was changed.

In Example 11, the same gas as above composed of the reaction product gas and the inert gas was introduced into a SUS 316 empty column-type collecting device having a diameter of 150 mm and a height of 5,000 mm and kept at a suitable temperature by an external jacket. A gas withdrawing port was provided at a position 4300 mm away from the gas inlet part.

The results are shown in Table 1 below.

The collected crystals were analyzed by liquid chromatography. For separation of pyromellitic anhydride, pyromellitic acid and pyromellitic monohydride, the crystals were subjected to fractional sterification treatment with methanol prior to analysis.

The ratio of crystal collection and the ratio of spontaneous crystal fall is the weight percent of the resulting crystals based on the weight of the resulting pyromellitic anhydride.

The ratio of adhesion of crystals to the wall surface is the difference between the ratio of crystal collection and the ratio of spontaneous crystal fall.

Hue (APHA) was evaluated with respect to 4-octyl pyromellitate (a plasticizer which is one important use of pyromellitic anhydride) prepared from the crystals of pyromellitic anhydride.

TABLE 1

| | Gas residence time (sec) | Average linear gas velocity (sec) | Collecting time (hr) | Rate of crystal collection (wt. %) | Rate of spontaneous fall of crystals (wt. %) | Rate of adhesion of crystals to the wall surface (wt. %) | Temperature of the outlet gas (°C.) | Temperature of the jacket (°C.) |
|---|---|---|---|---|---|---|---|---|
| Example 1 | 5.0 | 0.070 | 19.5 | 71.0 | 69.3 | 1.7 | 167 | 167 |
| Example 2 | 11.3 | 0.070 | 18.3 | 79.7 | 76.4 | 3.3 | " | " |
| Example 3 | 21.4 | 0.070 | 18.3 | 87.8 | 85.4 | 2.4 | " | " |
| Example 4 | 31.0 | 0.070 | 20.5 | 94.4 | 91.6 | 2.8 | " | " |
| Example 5 | 51.8 | 0.070 | 19.3 | 94.7 | 92.9 | 1.8 | " | " |
| Example 6 | 31.0 | 0.065 | 19.5 | 79.3 | 76.3 | 3.0 | 189 | 187 |
| Example 7 | " | 0.068 | 21.5 | 86.9 | 83.6 | 3.3 | 179 | 177 |
| Example 8 | " | 0.069 | 20.5 | 89.6 | 85.9 | 3.7 | 173 | 172 |
| Example 9 | " | 0.073 | 19.5 | 95.5 | 93.2 | 2.3 | 162 | 162 |
| Example 10 | " | 0.068 | 20.3 | 94.4 | 92.8 | 1.6 | 167 | 167 |
| Example 11 | 22.0 | 0.194 | 19.8 | 88.3 | 86.4 | 1.9 | " | " |
| Comparative Example | 33.0 | 0.045 | 21.3 | 95.4 | 31.5 | 63.9 | " | " |

| | Type of the inert gas | Flow rate of the cooling gas (N l/hr) | Appearance of the crystals | Hue (APHA) of 4-octyl pyromellitate | Analysis values (wt. %) by liquid chromatography | | | |
|---|---|---|---|---|---|---|---|---|
| | | | | | PMDA | PMMA | PMA | TMMA |
| Example 1 | Air | 2765 | White fine needle-like | 50 | 99.63 | 0.16 | 0.11 | 0.10 |
| Example 2 | " | " | " | 60 | 99.60 | 0.15 | 0.13 | 0.12 |

TABLE 1-continued

| | | | | | | | | |
|---|---|---|---|---|---|---|---|---|
| Example 3 | " | " | " | 60 | 99.64 | 0.14 | 0.10 | 0.10 |
| Example 4 | " | " | " | 60 | 99.62 | 0.15 | 0.12 | 0.11 |
| Example 5 | " | " | " | 60 | 99.58 | 0.16 | 0.13 | 0.13 |
| Example 6 | " | 1909 | " | 60 | 99.59 | 0.15 | 0.12 | 0.14 |
| Example 7 | " | 2358 | " | 60 | 99.61 | 0.16 | 0.11 | 0.12 |
| Example 8 | " | 2605 | " | 60 | 99.56 | 0.17 | 0.14 | 0.13 |
| Example 9 | " | 3153 | White yellow fine needle-like | 150 | 99.31 | 0.15 | 0.15 | 0.39 |
| Example 10 | Nitrogen | 2544 | White fine needle-like | 60 | 99.59 | 0.14 | 0.16 | 0.11 |
| Example 11 | Air | 2765 | " | 60 | 99.60 | 0.15 | 0.12 | 0.13 |
| Comparative Example | None | 0 | White needle-like | 70 | 99.61 | 0.15 | 0.11 | 0.13 |

Note
PMDA = pyromellitic anhydride (pyromellitic dianhydride)
PMMA = pyromellitic monoanhydride
PMA = pyromellitic acid
TMMA = trimellitic anhydride

What is claimed is:

1. A method of collecting pyromellitic anhydride, which comprises introducing a high-temperature gas containing pyromellitic anhydride together with an inert cooling gas into an empty column-type collecting device whose wall temperature is maintained at 150 to 200 C., effecting heat exchange between the high-temperature gas and the cooling gas in the collecting device to lower the temperature of the high-temperature gas to 150° to 200° C., thereafter passing the gaseous mixture through the collecting device at an average linear gas velocity of 0.05 to 0.5 m/sec with an average residence time to 5 to 60 seconds, and recovering needle-like crystals of pyromellitic anhydride from the bottom of the collecting device.

2. The method of claim 1 wherein the high-temperature gas containing pyromellitic anhydride is a product of catalytic vapor-phase oxidation reaction of a 1,2,4,5-tetraalkylbenzene with a molecular oxygen-containing gas.

3. The method of claim 1 wherein the high-temperature gas containing pyromellitic anhydride is a mixture of pyromellitic anhydride and an inert carrier gas formed at the time of purifying pyromellitic anhydride by sublimation.

4. The method of claim 1 wherein the inert cooling gas is air, nitrogen, carbon dioxide or argon.

5. The method of claim 1 wherein the inert cooling gas is a waste gas left after collecting pyromellitic anhydride from the catalytic vapor-phase oxidation reaction product.

* * * * *

UNITED STATES PATENT AND TRADEMARK OFFICE
CERTIFICATE OF CORRECTION

PATENT NO. : 4,725,291

DATED : February 16, 1988

INVENTOR(S) : UEOKA ET AL.

It is certified that error appears in the above-identified patent and that said Letters Patent is hereby corrected as shown below:

On the cover page of the patent the Foreign Application Priority Data has been omitted, therefore please insert the following data: --Foreign Application Priority Data, March 17, 1986[JP], Japan, 61-57091--.

Signed and Sealed this

Nineteenth Day of July, 1988

*Attest:*

DONALD J. QUIGG

*Attesting Officer*      *Commissioner of Patents and Trademarks*